(12) United States Patent
Smith

(10) Patent No.: US 10,813,879 B1
(45) Date of Patent: *Oct. 27, 2020

(54) HAIR CONDITIONER COMPOSITION

(71) Applicant: HauteHerbotique, LLC, Evanston, IL (US)

(72) Inventor: Marlene M. Smith, Evanston, IL (US)

(73) Assignee: Haute Herbotique, LLC, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,326

(22) Filed: Apr. 24, 2019

(51) Int. Cl.
| | |
|---|---|
| *A61K 8/9789* | (2017.01) |
| *A61K 8/92* | (2006.01) |
| *A61K 8/98* | (2006.01) |
| *A61Q 5/12* | (2006.01) |
| *A61K 8/60* | (2006.01) |
| *A61K 8/34* | (2006.01) |

(52) U.S. Cl.
CPC .............. *A61K 8/9789* (2017.08); *A61K 8/34* (2013.01); *A61K 8/60* (2013.01); *A61K 8/922* (2013.01); *A61K 8/925* (2013.01); *A61K 8/988* (2013.01); *A61Q 5/12* (2013.01); *A61K 2800/524* (2013.01); *A61K 2800/5922* (2013.01)

(58) Field of Classification Search
CPC ...... A61K 8/9789; A61K 8/922; A61K 8/925; A61K 8/988; A61K 8/60; A61K 8/34; A61K 2800/5922; A61K 2800/524; A61Q 5/12

See application file for complete search history.

(56) References Cited

U.S. PATENT DOCUMENTS

| | | | |
|---|---|---|---|
| 8,623,335 B2 | 1/2014 | Waddington | |
| 8,920,853 B2 * | 12/2014 | Darsale | ..................... A61Q 5/00 424/725 |
| 2015/0250707 A1 * | 9/2015 | Lee | ........................... A61Q 5/08 132/208 |

FOREIGN PATENT DOCUMENTS

| | | | |
|---|---|---|---|
| CN | 106580824 | * | 4/2017 |
| EP | 1609461 | * | 12/2005 |

OTHER PUBLICATIONS

Curlmix (Mar. 1, 2019).*
Ruggeri (Mar. 2017).*
Tay et al. (Jul. 2018).*
Science-y hair blog (2012).*
Crunchy (Jun. 19, 2017).*

* cited by examiner

*Primary Examiner* — Shirley V Gembeh
(74) *Attorney, Agent, or Firm* — Fay Sharpe LLP

(57) ABSTRACT

The present disclosure relates to a formulation of a shampoo conditioner composition comprising water, flaxseed, olive oil, jojoba oil, emu oil, honey, and preservatives. This composition provides desirable characteristics such as increased moisture and non-comedogenic effects.

10 Claims, No Drawings

HAIR CONDITIONER COMPOSITION

BACKGROUND

The present disclosure relates to compositions for use as hair conditioner.

Hair conditioner compositions vary regarding their desired properties. It would be desirable to provide a hair conditioner composition which has improved moisturizing, anti-frizz, styling, and non-comedogenic characteristics utilizing cost-effective ingredients.

BRIEF DESCRIPTION

Disclosed, in various embodiments, are shampoo conditioner compositions which provide desirable qualities to hair post-use. It is contemplated that these conditioner compositions can be used on both humans or pets (e.g. cats, dogs, or other animals).

In embodiments, the hair conditioner composition comprises a first portion of water and flaxseed, and a second portion of olive oil, jojoba oil, emu oil, honey, and preservatives. Regarding the second portion, the olive oil is the majority ingredient. Jojoba oil and emu oil are present in approximately equal amounts. Honey is the minority ingredient of the second portion. The volume ratio of olive oil to jojoba oil to emu oil to honey is approximately 48:4:4:1.

Chia seed and quince seed may be substituted for flaxseed in the first portion.

Grape seed oil, almond oil, or avocado oil may be substituted for olive oil in the second portion.

Molasses or agave may be substituted for honey in the second portion.

These and other non-limiting characteristics are more particularly described below.

DETAILED DESCRIPTION

The numerical values in the specification and claims of this application should be understood to include numerical values which are the same when reduced to the same number of significant figures and numerical values which differ from the state value by less than the experimental error of conventional measurement techniques of the type described in the present application to determine the value.

The present disclosure may be understood more readily by reference to the following detailed description of preferred embodiments and the examples included herein.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 1:2" also discloses the value "1:2" and the term "from about 2 to about 4" also discloses the range "from 2 to 4." The term "about" may refer to plus or minus 10% of the indicated number.

The components of the hair conditioner compositions of the present disclosure are water, flaxseed, olive oil, jojoba oil, emu oil, honey, and preservatives. The water and flaxseed comprise a first portion. Olive oil, jojoba oil, emu oil, honey, and preservatives comprise a second portion. The preservative system comprises an alcohol, xylitol, and lemon grass essential oil.

The scope of the present disclosure includes ingredients which contribute similar characteristics to the overall hair conditioner composition. Flaxseed may be replaced with chia seed or quince seed. Olive oil may be replaced by grape seed oil, almond oil, avocado oil, coconut oil, canola oil, sesame seed oil, or any similar oils. Emu oil serves to penetrate hair while exhibiting non-comedogenic properties. Additionally, emu oil exhibits anti-bacterial properties. Any oil imparting non-comedogenic, anti-bacterial, and other similar characteristics may be substituted for emu oil. Honey imparts moisturizing effects on the composition and imparts nutrients into the hair. Molasses or agave may be substituted for honey.

In embodiments, the volume ratio of flaxseed to olive oil, prior to preparation of the composition, is from approximately 1:1 to about 3:1. The volume ratio of olive oil to jojoba oil is from approximately 2:1 to about 6:1. The volume ratio of olive oil to emu oil is from approximately 2:1 to about 6:1. The volume ratio of olive oil to honey is from approximately 20:1 to about 80:1. The volume ratio of jojoba oil to emu oil is from approximately 1:2 to about 2:1. The volume ratio of olive oil to jojoba oil to emu oil to honey is approximately 48:4:4:1. Honey is the minority ingredient because increasing the amount of honey results in a composition with increased adhesiveness, which negatively affects hair upon application.

The preservation system is prepared separately from the other components of the composition. The components of the preservative system are an alcohol, xylitol, and an essential oil. The preservative system can also include water (considered separately from the water in the first portion of the conditioner composition).

The alcohol may be any suitable primary, secondary, or tertiary alcohol. Examples of alcohols may include methanol, ethanol, n-propyl alcohol, isopropyl alcohol, n-butyl alcohol, and tert-butyl alcohol. In particular embodiments, the alcohol is ethanol.

The xylitol can be provided in either powder or liquid form. Xylitol is a 5-carbon sugar that has anti-fungal and anti-microbial properties because it cannot be easily metabolized by fungi/bacteria. Salts and other forms of xylitol (e.g. the monoester) are contemplated as falling within the scope of this disclosure.

Suitable essential oils include essential oils of basil, bay leaf, cinnamon, eucalyptus, guava, oregano, rosemary, spearmint, tea tree, thyme, lemon grass (also known as cymbopogon), or combinations thereof. In particular embodiments, lemon grass essential oil is used. A small amount of essential oil is used, ranging from 15 to 25 drops (gtts) per 2.5 teaspoons of the preservative system. One milliliter is approximately equal to 15 to 20 drops.

The volume ratio of the alcohol to xylitol may be from about 2:1 to about 9:1. In particular embodiments, the volume ratio of the alcohol to xylitol is about 4.8:1. The volume ratio of the alcohol to the essential oil may be from about 7:1 to about 28:1. In particular embodiments, the volume ratio of the alcohol to the essential oil is about 14.4:1. The volume ratio of xylitol to the essential oil may be from about 2:1 to about 6:1. In particular embodiments, the volume ratio of xylitol to the essential oil is about 3:1.

When water is present, the volume ratio of water to the alcohol may be from about 3:1 to about 1:1. In particular embodiments, the water and the alcohol are added together in the form of vodka, which contains ethanol and is typically 40% alcohol by volume (ABV). The water and the alcohol together generally provide from about 60 vol % to about 90 vol % of the system.

The volume ratio of water to alcohol to xylitol to essential oil may be, in particular embodiments, about 21.6:14.4:3:1.

Put another way, the amount of essential oil is very small relative to the amount of water, the alcohol, and xylitol. Any combination of these volume ratios is contemplated for the preservative system.

The hair conditioner composition may be made by boiling water and flaxseed for approximately 20 minutes, yielding about 200 mL of gel after any excess liquid is strained off. Olive oil, jojoba oil, emu oil, honey, and the preservatives are then added to the gel. It is noted that the volume ratio of the preservative system to the rest of the ingredients is generally from about 5:7 to about 7:7.

The following example is provided to illustrate the composition of the present disclosure. The example is merely illustrative and is not intended to limit the disclosure to the materials, conditions, or process parameters set forth therein.

EXAMPLE 1

Four tablespoons of flaxseed was boiled in 2 cups of water for 20 minutes, yielding approximately 200 mL of gel after excess liquid was strained off.

A preservative system was made by combining:
2 tablespoons of vodka;
½ teaspoon of xylitol; and
20 gtts of lemon grass essential oil.

The following ingredients were added to the 200 mL of gel:
2 tablespoons of olive oil;
½ teaspoon of jojoba oil;
½ teaspoon of emu oil;
⅛ teaspoon of honey; and
the preservative system.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A hair conditioner composition, comprising a first portion and a second portion, wherein:
the first portion comprises a gel; and
the second portion comprises olive oil, jojoba oil, emu oil, a non-comedogenic substance, and a preservative system;
wherein the volume ratio of olive oil to jojoba oil is from approximately 2:1 to about 6:1; and
wherein the volume ratio of olive oil to emu oil is from approximately 2:1 to about 6:1.

2. The composition of claim 1, wherein the gel comprises water and flaxseed.

3. The composition of claim 1, wherein the gel comprises water and chia seeds.

4. The composition of claim 1, wherein the gel comprises water and quince seeds.

5. The composition of claim 1, wherein the volume ratio of jojoba oil to emu oil is from approximately 1:2 to about 2:1.

6. The composition of claim 1, wherein the volume ratio of olive oil to the non-comedogenic substance is from approximately 20:1 to about 80:1.

7. The composition of claim 1, wherein the non-comedogenic substance is honey.

8. The composition of claim 1, wherein the preservative system comprises:
vodka;
xylitol; and
lemon grass essential oil.

9. A hair conditioner composition, comprising a first portion and a second portion, wherein:
the first portion comprises water and flaxseed;
the second portion comprises olive oil, jojoba oil, emu oil, honey, and preservatives; and
the volume ratio of flaxseed to olive oil to jojoba oil to emu oil to honey is approximately 96:48:4:4:1.

10. A method for making hair conditioner composition, comprising:
preparing a first portion by boiling water and flaxseed to create a gel;
preparing a second portion, the second portion comprising olive oil, jojoba oil, emu oil, honey, and preservatives;
wherein the preservatives comprise vodka, xylitol, and lemon grass essential oil; and
combining the first portion and the second portion.

* * * * *